United States Patent [19]

Bowers et al.

[11] Patent Number: 5,661,226

[45] Date of Patent: *Aug. 26, 1997

[54] HIGH SENSITIVITY REAL-TIME NVR MONITOR

[75] Inventors: William D. Bowers, Newport Beach, Calif.; Raymond L. Chuan, Hanalei, Hi.

[73] Assignee: Femtometrics, Irvine, Calif.

[*] Notice: The term of this patent shall not extend beyond the expiration date of Pat. No. 5,476,002.

[21] Appl. No.: 554,893

[22] Filed: Nov. 9, 1995

Related U.S. Application Data

[60] Division of Ser. No. 238,479, May 5, 1994, Pat. No. 5,476,002, which is a continuation-in-part of Ser. No. 95,930, Jul. 22, 1993, abandoned.

[51] Int. Cl.$^6$ ................................................. G01N 29/02
[52] U.S. Cl. .............................................................. 73/24.01
[58] Field of Search ................................ 73/24.01, 24.05, 73/24.06, 31.05, 31.06; 310/313 R, 313 B, 313 D

[56] References Cited

U.S. PATENT DOCUMENTS

| | | | |
|---|---|---|---|
| 3,715,911 | 2/1973 | Chuan | 73/24.03 |
| 4,307,356 | 12/1981 | Arai | 310/313 D |
| 4,518,944 | 5/1985 | Faris | 310/343 |
| 4,561,286 | 12/1985 | Sekler et al. | 73/24.06 |
| 4,596,697 | 6/1986 | Ballato | 422/98 |

(List continued on next page.)

FOREIGN PATENT DOCUMENTS

| | | |
|---|---|---|
| 4148844 | 5/1992 | Japan . |
| 1681229 | 9/1991 | U.S.S.R. . |

OTHER PUBLICATIONS

White, et al., "Direct Piezoelectric Coupling to Surface Elastic Waves", *Applied Physics Letter*, vol. 7, No. 12, Dec. 15, 1965, pp. 314–316.

Wohltjen, et al., "Surface Acoustic Wave Probe for Chemical Analysis. I. Introduction and Instrument Description", *Analytical Chemistry*, vol. 51, No. 9, Aug. 1979, pp. 1458–1464.

(List continued on next page.)

*Primary Examiner*—Michael Brock
*Attorney, Agent, or Firm*—Knobbe, Martens, Olson & Bear LLP

[57] ABSTRACT

A real time non-volatile residue (NVR) monitor, which utilizes surface acoustic wave (SAW) resonators to detect molecular contamination in a given environment. The SAW resonators operate at a resonant frequency of approximately 200 MHz–2,000 MHz which enables the NVR monitor to detect molecular contamination on the order of $10^{-11}$ g-cm$^{-2}$ to $10^{-13}$ g-cm$^{2}$. The NVR monitor utilizes active temperature control of (SAW) resonators to achieve a stable resonant frequency. The temperature control system of the NVR monitor is able to directly heat and cool the SAW resonators utilizing a thermoelectric element to maintain the resonators at a present temperature independent of the environmental conditions. In order to enable the direct heating and cooling of the SAW resonators, the SAW resonators are operatively mounted to a heat sink. In one embodiment, the heat sink is located in between the SAW resonators and an electronic circuit board which contains at least a portion of the SAW control electronics. The electrical leads of the SAW resonators are connected through the heat sink to the circuit board via an electronic path which prevents inaccurate frequency measurement.

14 Claims, 7 Drawing Sheets

U.S. PATENT DOCUMENTS

| | | |
|---|---|---|
| 4,599,532 | 7/1986 | Okamoto et al. ................ 310/313 D |
| 4,683,394 | 7/1987 | Koshino ........................... 310/313 D |
| 4,792,939 | 12/1988 | Hikita et al. ............................ 370/24 |
| 4,895,017 | 1/1990 | Pyke et al. ............................ 73/24.06 |
| 4,917,499 | 4/1990 | Champetier et al. .................. 374/14 |
| 4,932,255 | 6/1990 | Brace et al. ......................... 73/24.03 |
| 5,042,288 | 8/1991 | Vig ....................................... 73/24.03 |
| 5,076,094 | 12/1991 | Frye et al. ............................ 73/24.06 |
| 5,117,146 | 5/1992 | Martin et al. ........................ 73/24.01 |
| 5,175,711 | 12/1992 | Shiba et al. ...................... 310/313 D |
| 5,194,830 | 3/1993 | Fleischmann ................... 310/313 D |
| 5,221,871 | 6/1993 | Fuchs et al. ......................... 73/24.01 |
| 5,223,762 | 6/1993 | Masaie et al. .................... 310/313 D |
| 5,289,715 | 3/1994 | Staples et al. ...................... 73/24.01 |
| 5,476,002 | 12/1995 | Bowers et al. ..................... 73/24.01 |

OTHER PUBLICATIONS

Wohltjen, et al., "Surface Acoustic Wave Probes for Chemical Analysis. II. Gas Chromatography Detector", *Analytical Chemistry*, vol. 51, No. 9, Aug. 1979, pp. 1465–1475.

Wohltjen, et al. "Surface Acoustic Wave Probes for Chemical Analysis. III Thermomechanical Polymer Analyzer", *Analytical Chemistry*, vol. 51, No. 9, Aug. 1979, pp. 1470–1475.

Wallace, "Miniature Quartz Crystal Microbalance for Contamination Measurement", *Journal of Spacecraft and Rockets*, vol. 17, No. 2, Mar.–Apr. 1980, pp. 153–156.

Wohltjen, "Mechanism of Operation and Design Considerations for Surface Acoustic Wave Device Vapour Sensors", *Sensors and Actuators*, vol. 5, 1984 pp. 307–325.

Whitehead, et al., "KSC Payload Facility Contamination Control Requirements/Plan", *National Aeronautics and Space Administration*, K–STSM–14.2.1, Rev. A, Nov. 1987.

Bowers, et al., "Surface Acoustic–Wave Piezoelectric Crystal Aerosol Mass Microbalance", *Rev. Sci. Instrum.*, vol. 60, No. 7, Jul. 1989, pp. 1297–1302.

Bowers, et al., "A 200 MHz Surface Acoustic Wave Resonator Mass Microbalance", *Rev. Sci. Instrum.*, vol. 62, No. 6, Jun. 1991, pp. 1624–1629.

Bowers, et al., "A High Sensitivity Real–Time NVR Monitor", *SPIE Proceedings on Optical System Contamination: Effects, Measurement, Control III*, vol. 1754, Jul. 23–24, 1992, pp. 344–351.

"Research and Technology 1993 Annual Report of the John F. Kennedy Space Center", *NASA Technical Memorandum 109200*, Dec. 1993, pp. 132–133.

Liang, et al., "Real–Time Saw Measurements of NVR in Cleanroom and in Microenvironmetn", *Proceedings from the Institute of Environmental Sciences 40th Annual Technical Meeting and Exposition*, May 1, 1994, 10 pages.

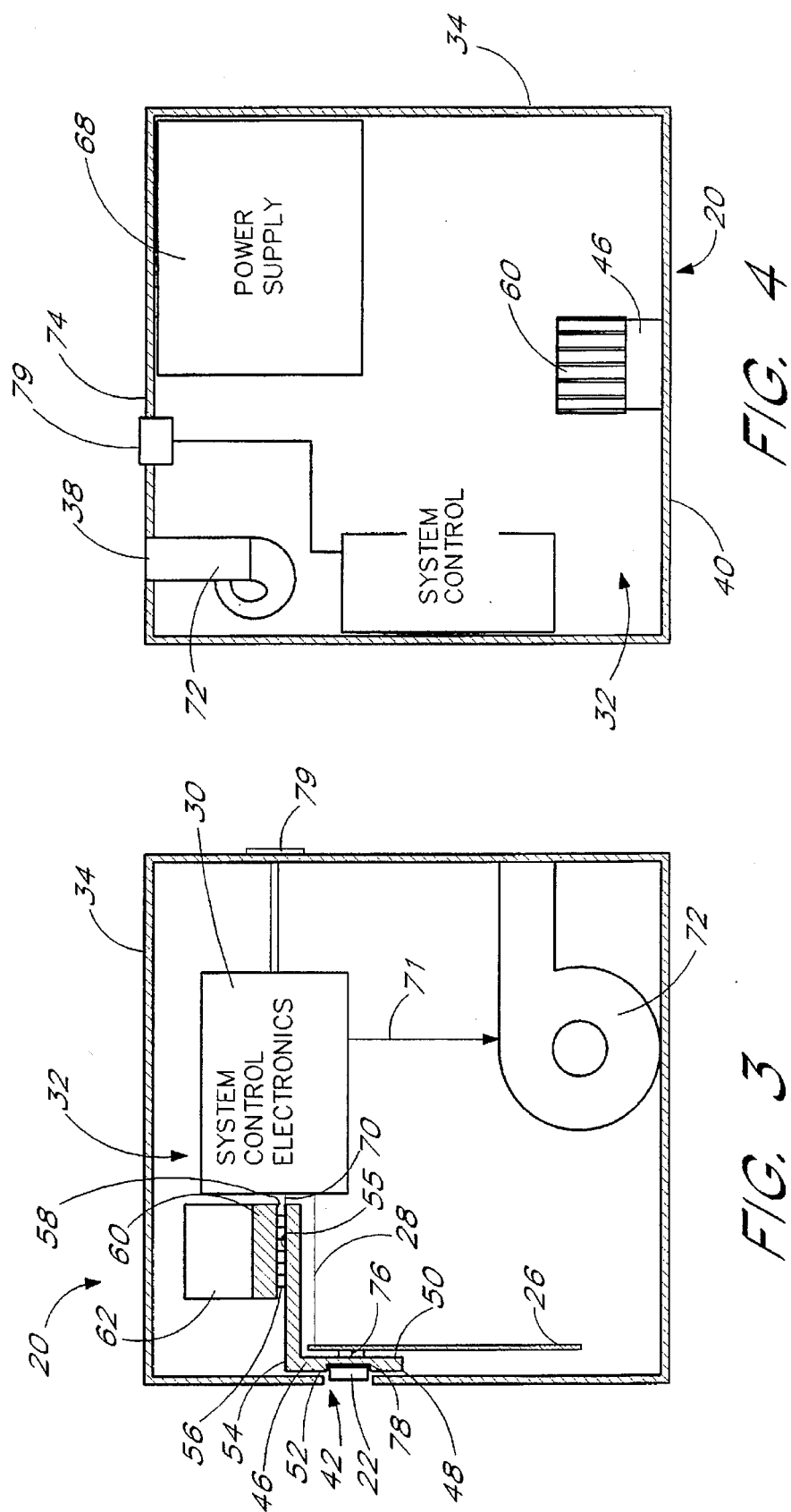

HIGH SENSITIVITY REAL-TIME NVR MONITOR

RELATED APPLICATION

This application is a division of U.S. patent application Ser. No. 08/238,479, filed May 5, 1994, now U.S. Pat. No. 5,476,002, which is a continuation-in-part of U.S. patent application Ser. No. 08/095,930, filed Jul. 22, 1993 now abandoned.

This invention was made with government support under contract NA10-11865 awarded by NASA. The government has certain rights in this invention.

BACKGROUND OF THE INVENTION

1. Field of the Invention

The present invention relates to a real time contamination monitor, more specifically, a contamination monitor which is capable of measuring contamination at the molecular level.

2. Description of the Related Art

The cleanliness requirements for the manufacture and operation of sophisticated technical systems are becoming ever more stringent. This is especially true in the manufacturing processes involved in microelectronics, high precision optics, as well as in the preparation of these types of systems for flight of spacecraft. It is no longer sufficient just to maintain a certain level of particle matter in a work environment, as has been the practice for several decades; it is becoming clear that contamination on a molecular level can create serious manufacturing and operational problems.

It is well known that all materials and most activities emanate gases or small aerosols by diffusion and desorption. The term "contamination" is applied when the emitted gas or aerosol impinges and condenses on a subject surface. Contamination of a "clean" surface orginates from two main sources: activities or processes in the clean work area and from the materials used in the construction of the article itself (self-induced contamination).

Non-volatile residue, (NVR), sometimes referred to as molecular contamination, on critical surfaces surrounding space structures have been shown to have a dramatic impact on the ability to perform optical measurements from platforms based in space with the particulate and NVR contamination originating primarily from pre-launch operations. Molecular deposition on surfaces affects the thermal balance of a spacecraft scheduled for a long duration mission since the absorptance and emittance of the thermal control panels are adversely affected. Any optical surface (such as windows or mirrors) is degraded by molecular depositions and particulates. Condensed fills of contaminants on the order of 10 angstroms thick degrade the efficiency and operation of the optical components. Therefore, a real-time measurement of NVR is required to assure that critical components are fully operational and not subjected to high levels of contaminants during payload processing and storage.

The pre-launch NVR contamination problem is even greater with the proposed Space Station since the large surface area of this structure would contribute significantly to the molecular contamination and could jeopardize the operation of numerous scientific instruments planned for this mission.

The currently accepted method of measuring NVR is the use of witness plates to collect the NVR over a time period up to several weeks. The major drawback to this technique is that the NVR contamination is integrated which precludes the real-time identification of a contamination event and the ability to curtail activities in the area which causes contamination. The method is also time consuming and tedious since a technician must wash the plates with a suitable solvent to remove the residue, filter the extract and place it in a pre-weighed dish which is then brought to dryness. The weight of the remaining residue is considered NVR and is expressed as $mg/0.1\ m^2$/month. A sensitive real-time NVR monitor would be a valuable instrument to reduce the overall level of contamination since activities which generate high levels of NVR would be detected in real-time and corrective measures can be taken in a timely manner.

More recently, the piezoelectric crystal microbalance has been used for the measurement of surface deposition on the particle level. Piezoelectric crystals in this category have operated in the bulk-vibration mode wherein the entire body of the crystal is driven electrically into resonance. The piezoelectric crystal operates as a microbalance by the de-tuning of the crystal's resonant frequency when mass is added to its surface.

U.S. Pat. No. 4,561,286 issued to Selker, et at. discloses such a bulk piezoelectric crystal microbalance. The bulk-vibration method requires the placement of the resonating electrodes on the opposite side of the bulk crystal, wherein the distance between the electrodes, i.e., the thickness of the crystal, defines the resonating frequency of the crystal. Therefore, the resonant frequency of a bulk vibration crystal is inversely proportional to the crystal thickness. The limit of the resonant frequency that can be obtained with a bulk mode crystal is approximately 15 MHz, because a thinner crystal would be manageable and therefore is not produced. Since the change in mass detectable by the crystal is proportional to the square of its frequency, the limit of mass resolution in the bulk vibration mode is typically on the order of $10^{-9}$ to $10^{-8}$ $g\text{-}cm^{-2}$. This level of mass resolution is sufficient to detect contamination at a particle level but is not fine enough to detect contamination at a molecular level.

Therefore, there exists a need for a real time piezoelectric monitor to measure contamination at a molecular level which can detect changes in mass due to molecular contamination on the order of $10^{-11}$ to $10^{-13}$ $g\text{-}cm^{-2}$ levels.

SUMMARY OF THE INVENTION

The present invention comprises a real time NVR monitor, or molecular contamination monitor, which utilizes surface acoustic wave (SAW) resonators connected to SAW control electronics. The resonators are used to detect the level of molecular contamination that is present in a given environment. The preferred embodiment of the NVR monitor utilizes a resonator with a resonant frequency of about 200 MHz–2,000 MHz which enables the NVR monitor to detect molecular contamination on the order of $10^{-11}$ $g\text{-}cm^{-2}$ to $10^{-13}$ $g\text{-}cm^{2}$.

Preferably, the NVR monitor utilizes active temperature control of the surface acoustic wave (SAW) resonators to reduce or eliminate thermally induced noise, increasing the stability of the resonator and improving the lower limit of detection. The temperature control system of the NVR monitor is able to directly heat and cool the SAW resonators utilizing a thermoelectric element to maintain the resonators at a selected temperature independent of the environmental conditions.

In order to enable the direct heating and cooling of the SAW resonators, the SAW resonators are operatively mounted to a heat sink, such that a first side of the heat sink is in thermal contact with the SAW resonators. The opposite side of the heat sink is proximal to at least a portion of the SAW control electronics (e.g., oscillator electronics). In one embodiment, the SAW control electronics are embodied in an electronic circuit board. As used herein, the term "electronic circuit board" includes a conventional circuit board in the event that conventionally packaged components are used for the SAW control electronics, and includes a hybrid substrate in the event that a hybrid circuit is used for these electronics. The preferred embodiment of the heat sink comprises two legs which are joined together at a right angle to form an L-shaped heat sink. One leg of the heat sink extends between the SAW resonators and the circuit board as described above. The other leg of the heat sink extends past the edge of the circuit board and is in thermal contact with a first side of a thermoelectric element, such as a peltier device. The thermoelectric element acts as both a heating element and as a cooling element depending on the direction of the current which is input to the thermoelectric element. An opposite side of the thermoelectric element is in contact with a radiator which assists in the dissipation of excess heat through metal cooling fins when the thermoelectric element is operating in the cooling mode.

As described above, the heat sink is positioned between and proximal to both the SAW resonators and at least a portion of the SAW control electronics. Electrical leads of the SAW resonators are connected to such SAW control electronics via an electrical path that extends through the heat sink. Such SAW resonators and electronics are in close proximity to prevent inaccurate frequency measurement from occurring due to impedance mismatching therebetween, losses in the electrical path and phase shifts in the frequency signal which are both caused by electrical paths of extended lengths. In the preferred embodiment, the heat sink has a recess in which the SAW resonators are mounted so as to decrease the length of the electrical path without significantly effecting the thermal conduction capacity of the heat sink. The length of the electrical path between the SAW resonators and the proximal portion of the SAW control electronics should be no more than 0.25 inches, and preferably approximately 0.1 to 0.2 inches in length.

In an alternate embodiment, another portion of the SAW control electronics is located remotely from the SAW resonators. The remotely located portion of the SAW electronics comprises signal processing electronics connected to the proximal portion of the SAW control electronics by an electrical conductor (e.g., wire). In another embodiment, the signal processing electronics are connected to the proximal portion of the SAW control electronics by optical fiber.

These and other features and advantages of the present invention are set forth more completely in the accompanying drawings and the following description.

BRIEF DESCRIPTION OF THE DRAWINGS

FIG. 3 is a somewhat schematic view taken in cross section along the lines 3—3 of FIG. 2.

FIG. 4 is a somewhat schematic view taken in cross section along the lines 4—4 of FIG. 2.

Detailed Description of the Preferred Embodiment

Figure 1:
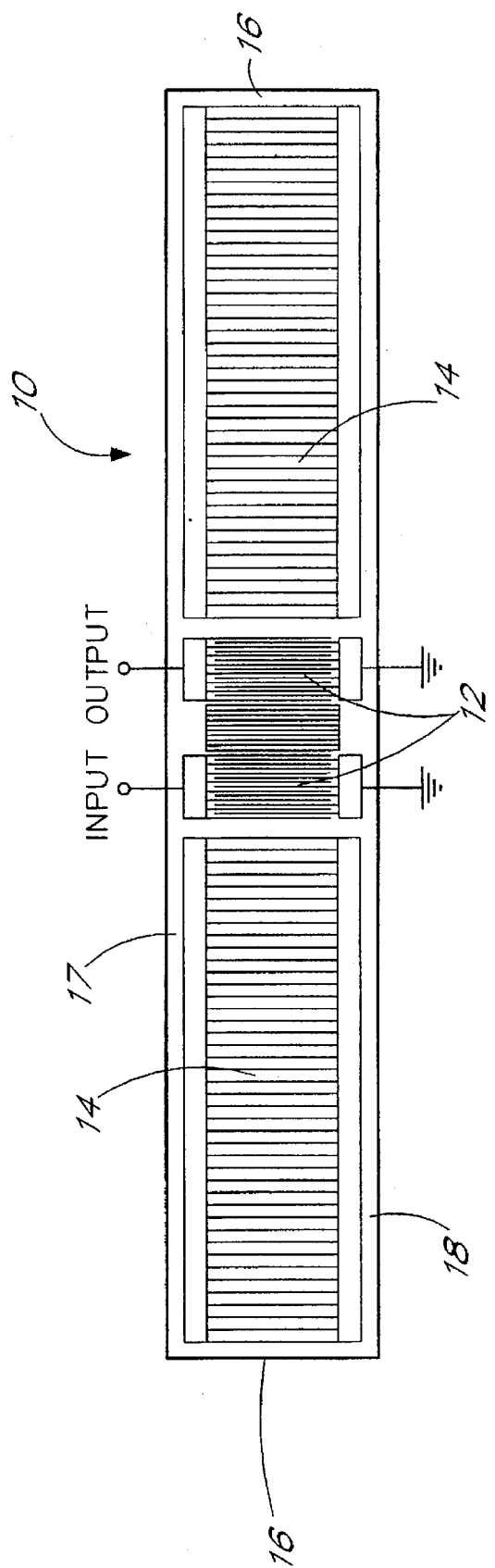
FIG. 1 is a schematic illustration of a SAW resonator which is utilized in the preferred embodiment of the NVR monitor of the present invention.

The present invention in its preferred embodiment comprises a real time NVR monitor which is capable of detecting molecular contamination on the order of $10^{-11}$ g-cm$^{-2}$ to $10^{-13}$ g-cm$^{-2}$. In order to obtain a mass resolution on this order, a piezoelectric crystal of a higher resonating frequency than the standard 10 MHz bulk vibration crystal is used. The relationship between frequency and mass may be defined mathematically. For example, the change in frequency due to mass addition $\Delta M$, over area A, follows the general form, $$\Delta f = -f_o^2 \Delta M/A \qquad (1)$$

The coefficient $\alpha$ depends on the type of crystal and the mode in which its oscillation is excited by the application of an electric field. For a quartz crystal operating in the thickness-shear mode (for an AT-cut bulk crystal), $$\Delta f = -2.2 \times 10^{-6} f_o^2 \Delta M/A \qquad (2)$$

Since the mass sensitivity is a function of the square of the operating frequency, small increases in the operating frequency give greater performance. However, with the standard bulk crystal operating in the shear mode, as the operating frequency increases, the thinner the crystal must be. A trade-off of mass sensitivity versus crystal ruggedness results in a 10 MHz crystal being the most commonly used as a microbalance as it possesses acceptable mechanical strength with a mass sensitivity around $4.42 \times 10^{-9}$ gm/Hz cm$^2$ (equivalent to $2.3 \times 10^8$ Hz cm$^2$/gm).

Higher resonating frequencies can be achieved by driving the crystal in a surface acoustic mode, wherein the top few atomic layers of the piezoelectric crystals surface are driven in a longitudinal acoustic mode by a series of closely spaced interdigitated electrode transducers which are deposited on the surface of the crystal substrate. The electric field is applied parallel to the surface of the crystal and Rayleigh waves are generated which move along the surface of the crystal. The fundamental frequency of this device is mainly dependent on the configuration of the transducers and not on the thickness of the substrate. Therefore, higher operating frequencies can be achieved without reducing the thickness of the crystal.

Surface acoustic wave (SAW) piezoelectric sensors typically used by researchers in analytical applications are based on SAW delay lines. When two sets of interdigital electrodes are deposited on a piezoelectric crystal at a distance L apart, a standing wave is set up if $L=N\lambda$, where N is an integer and $\lambda$ is the wavelength of the surface acoustic wave. The frequency f is equal to $v/\lambda$, where v is the surface acoustic wave phase velocity. The wavelength is dependent on the spacing, s, between the interdigital electrodes, and is equal to twice the spacing. The bandwidth of the device is determined by the length of each transducer. The transducers serve two main functions, the first is to convert electrical energy from the oscillator circuit into mechanical energy on the surface of the quartz piezoelectric crystal, and vise versa. The second function is to establish the frequency response of the delay line. The Rayleigh surface wave travels in both directions away from the transducer. The surface wave that travels away from the opposite transducer and towards the end of the crystal is lost which results in the delay line being a low Q device.

There are several limitations of the SAW delay lines which necessitated the development of a new type of SAW piezoelectric microbalance using an alternative SAW configuration, called a SAW resonator. FIG. 1 illustrates a SAW resonator 10 which is utilized in the NVR monitor of the preferred embodiment. Preferably, a SAW resonator operates at a resonant frequency of approximately 200 MHz–2,000 MHz. The SAW resonator 10 is constructed in accordance with methods similar to those disclosed in an article entitled "A 200 MHz Surface Acoustic Wave Resonator Mass Microbalance", by W. D. Bowers and R. L. Chuan, published in Rev. Sci. Instrum., Vol. 62, pp. 1624 in 1991, which is hereby incorporated by reference. The SAW resonator 10 is similar in construction to a standard SAW delay line with interdigital electrodes deposited onto the surface of an ST quartz substrate, but contains additional passive elements deposited on its surface. The SAW resonator 10 consists of two transducer electrode arrays 12 that convert the electrical energy into mechanical energy and a set of reflector arrays 14 on each end 16 of the crystal 17. Unlike the delay line, the resonator's frequency of oscillation is determined by the configuration of the reflector arrays 14. The mechanical energy traveling along the surface 18 of the crystal 17 is reflected back towards the transducer 12 setting up a standing wave trapping the acoustic energy within the crystal 17 by the constructive interference of the reflected waves. The resonator 10 is therefore a high Q device since the energy is not lost on the ends 16 of the crystal 17. When a SAW resonator 10 of approximately 200 MHz (e.g., 199.1 MHz) is utilized, the NVR monitor 20 has a mass sensitivity of $2 \times 10^{-11}$ gm/Hz cm$^2$/gm (equivalent to 50 Hz cm$^2$/gm).

The inherent noise of an instrument is typically one of the major parameters in determining the lower limit-of-detection as it directly relates to the signal-to-noise ratio. For the SAW resonator 10, this is the frequency variation or "background noise". Depending on the application, microgravimetric measurements can be made over a period as short as several seconds or up to several weeks or months. The limit-of-detection is a function of both the mass sensitivity of the crystal, which is determined by the operating frequency, and the background noise of the system. In order to obtain the lowest minimal detectable mass for a given operating frequency the background noise, or frequency fluctuation, of the SAW resonator 10 must be as low as possible.

The frequency stability, $\delta f/f$, of a 200 MHz SAW resonator 10 is an order of magnitude better than a conventional 10 MHz bulk crystal and a tremendous improvement over a 158 MHz delay line system. With a frequency stability better than $5 \times 10^{-9}$, an absolute mass sensitivity of $2 \times 10^{-11}$ gm/Hz cm$^2$ and an active surface area of 0.1 cm$^2$, the lower limit-of-detection (assuming a S/N of 3) of a 200 MHz SAW resonator is approximately $6 \times 10^{-12}$ grams which is close to three orders of magnitude lower than a 10 MHz temperature controlled quartz crystal microbalance (TQCM).

Referring to FIGS. 2–6, the preferred embodiment of the NVR monitor 20 of the present invention preferably operates in the dual difference mode (as typically done with the conventional QCM). In the dual difference mode, two SAW resonators are used, a first sensing resonator 22, also referred to as a detection resonator, and a second reference resonator 24. The sensing resonator 22 is exposed to the environment to measure the NVR contamination that is deposited on its surface. The reference resonator 24 is hermetically sealed in a standard electronics package to prevent any contamination from effecting its resonant frequency. Preferably, the reference resonator 24 is matched to the sensing resonator 22 to ensure that the reference resonator 24 has a resonating frequency which is approximately 10 KHz to 100 KHz above the frequency of the sensing resonator 22.

FIGS. 2–5 illustrate embodiments in which the resonators 22, 24 are connected to SAW control electronics 25 embodied in an electronic circuit board 26. An output signal from the sensing resonator 22 is mixed with an output signal from the reference resonator 24 on the electronic circuit board 26 which contains the SAW control electronics 25 and the difference or beat frequency is determined and supplied as an output signal to system control electronics 30 via a line 28. By selecting the reference resonator 24 to be at a frequency which is above the frequency of the sensing resonator 22, a decrease in frequency of the sensing resonator 22, due to the deposition of molecules on its surface, is manifested as an increase in the beat frequency from the SAW control electronics 25 on the electronic circuit board 26.

Figure 6:
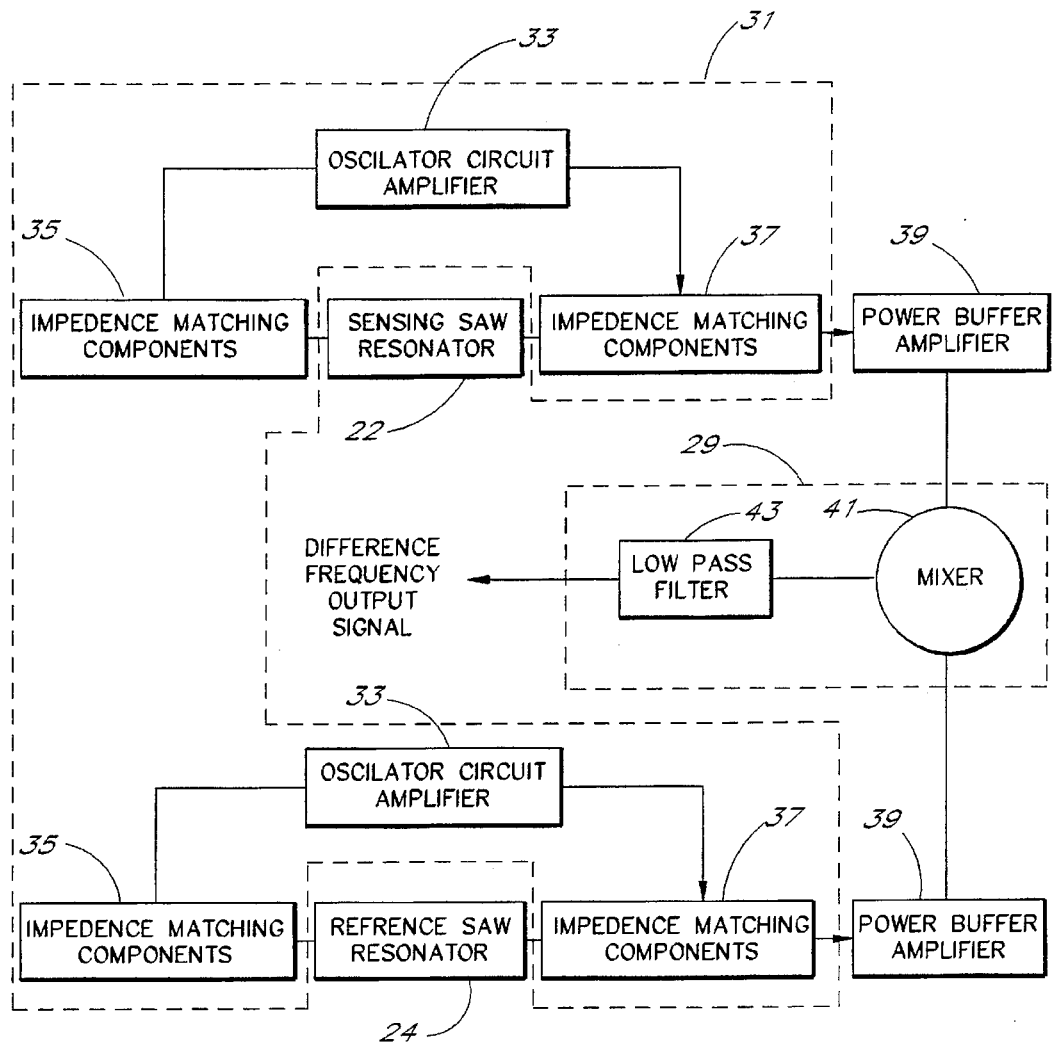
FIG. 6 is a block diagram of the SAW control electronics.

As illustrated in FIG. 6, the SAW electronics 25 may comprise signal processing electronics 29 and oscillator electronics 31. The oscillator electronics 31 comprises, for each of the resonators 22, 24, an oscillator circuitry amplifier 33, a first set of impedance matching components 37 and a second set of impedance matching components 35. The operation of the oscillator electronics 31 will be described hereinafter with reference to the sensing resonator 22; however, it will be understood that a similar set of electronic components are provided for the reference resonator 24 and that these components operate in the same way. In this regard, the oscillator circuit amplifier 33 amplifies the output signal from the sensing resonator 22 to accommodate any signal losses. The output signal from the oscillator circuit amplifier 33 is fed back to the sensing resonator 22 through the first set of impedance matching components 37. The first set of impedance matching components 37 comprises passive components (inductors, capacitors, resistors, etc.), which match the signals from the oscillator circuit amplifier 31 to the input characteristics of the sensing resonator 22 and power buffer amplifier 39. The power buffer amplifier 39 connects each portion of the oscillator electronics 31 to the signal processing electronics 29. A second set of impedance matching components 35 comprises passive components (inductors, capacitors, resistors, etc.), which match the signal from the resonator 22 with the input characteristics of the oscillator circuit amplifier 31. In addition, the power buffer amplifier 39 provides isolation for the oscillator electronics 31 from the signal processing electronics 29. The signal processing electronics 29 comprises a mixer 41, and a low pass filter 43. The output of the signal processing electronics 29 is a difference or beat frequency which is supplied to the system control electronics 30. As discussed hereafter, the system control electronics 30 includes temperature control electronics and signal conducting electronics.

Figure 2:
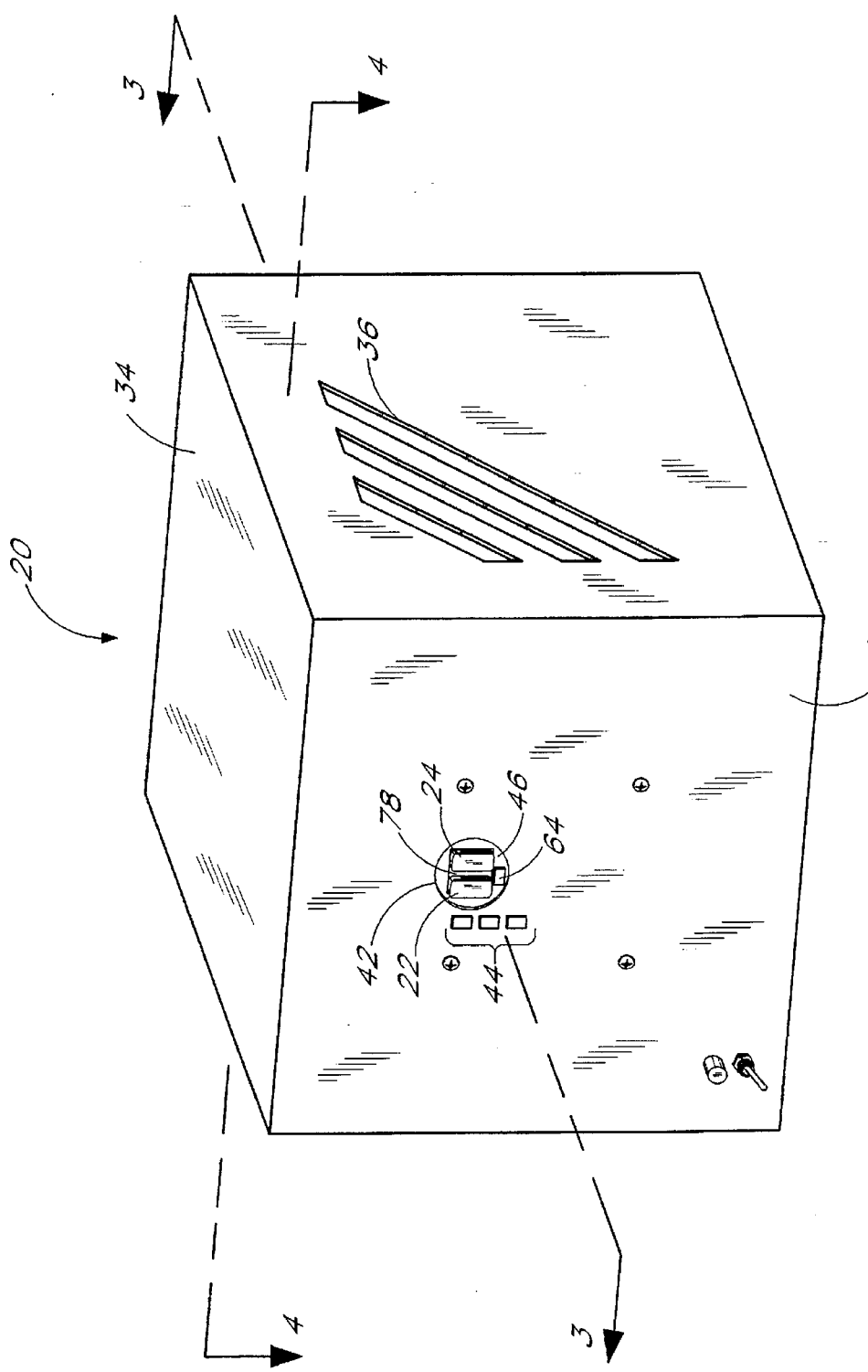
FIG. 2 is a perspective view of a preferred embodiment of the NVR monitor of the present invention.

As best illustrated in FIG. 2, the reference resonator 22 is mounted proximal to the sensing resonator 24. Both resonators are thus exposed to the same environmental conditions, which automatically compensates for fluctuations in temperature and pressure caused by the environment in which the SAW resonators 22, 24 are located. In addition, by measuring only the beat frequency rather than the individual frequency of the resonators 22, 24, the resulting beat frequency signal is in the kilohertz range which can be acquired with conventional data acquisition hardware rather than requiting special equipment to measure and transmit the high order frequencies of the individual resonators 22, 24.

Although using a reference resonator 24 in the dual difference mode to correct for temperature fluctuations drastically reduces frequency fluctuations at least three orders of magnitude, it does not eliminate it completely. Common fluctuations in room temperature, several ° C. over an hour or so, do not induce a significant drift in the instruments baseline signal. However, since it may require several days to weeks to measure extremely low levels of NVR contamination any temperature induced drift must be eliminated (preferably) or corrected for drift via a calibration curve for each sensor.

In order to guard against false NVR readings due to drastic changes in the environment temperature, the temperature of the SAW resonators 22, 24 is actively controlled apart from the temperature fluctuations in the surrounding environment. By actively controlling the temperature of the SAW resonators 22, 24 to maintain a preset or preselected temperature, temperature changes in the environment will not induce a major drift in the baseline temperature. In this way, the theoretical lower limit-of-detection of a 200 MHz SAW resonator 10, i.e., mass detection on the order of $10^{-11}$ g-cm$^{-2}$, can be realized. In order to accurately control the temperature of the SAW resonators 22, 24, the NVR monitor 20 includes temperature control components 32 comprising a heat sink 46, a thermal electric element 56, a radiator 60, a temperature sensor 64 and temperature control electronics which are a part of the system control electronics 30. The temperature control system 32 is able to directly heat and cool the SAW resonators 22, 24 to maintain the resonators at a preset temperature independent of the environmental conditions.

In one preferred embodiment, shown in FIGS. 2–4, all of the operating elements of the real-time NVR monitor 20 are housed within a single enclosure 34 which is sealed from the environment except for an air vent 36 and a ventilation duct 38 which enable the cooling of the operational elements of the NVR monitor 20. A front face 40 of the enclosure 34 includes an aperture 42 through which the reference and the sensing SAW resonators 22, 24 are exposed to the external environment. Also on the front face 40 of the enclosure proximal to the resonators 22, 24 is an array of environmental sensors 44 which monitor certain parameters that may influence the manner in which the NVR monitor 20 operates, such as room temperature, humidity, etc. In order to enable the direct heating and cooling of the SAW resonators 22, 24, the SAW resonators 22, 24 are operatively mounted to a heat sink 46, such that a first side 48 of the heat sink 46 physically and thermally contacts the SAW resonators 22, 24. The opposite side 50 of the heat sink 46 is proximal to the electronic circuit board 26 which contains the SAW control electronics 25.

The preferred embodiment of the heat sink 46 comprises legs 52, 54 which are joined together at a right angle to form an L-shaped heat sink 46. The leg 52 of the heat sink 46 extends between the SAW resonators 22, 24 and the electronic circuit board 26. The leg 54 of the heat sink 46 extends past the electronic circuit board 26 and physically contacts a first side 55 of a thermoelectric element 56, such as a peltier device. An opposite side 58 of the thermoelectric element 56 is in physical contact with a radiator 60 which assists in the dissipation of excess heat through metal cooling fins 62.

The thermoelectric element 56 is used to control the temperature of the SAW resonators 22, 24. The operation of the thermoelectric element 56 is controlled by temperature control electronics which are a part of the system control electronics 30. The thermoelectric element 56 acts as both a heating element and as a cooling element depending on the direction of the current which is input to the thermoelectric element 56. If the current is applied in a forward direction, i.e. toward a positive voltage terminal of the thermoelectric element 56, the thermoelectric element 56 acts as a thermal heater. If the current is applied in a backwards direction, i.e., towards a negative voltage terminal of the thermoelectric element 56, the thermoelectric element 56 acts as a thermal cooler. The magnitude of the current which is sent to the thermoelectric element 56 determines the magnitude of the heating or cooling of the SAW resonators 22, 24. The temperature control electronics receives the SAW temperature information from a temperature sensor 64 which is mounted on the heat sink 46 in dose proximity to the SAW resonators 22, 24. The temperature detected by the temperature sensor 64 is compared to a stored preset temperature which is the preferred operating temperature of the NVR monitor 20 for a given application. As the NVR monitor 20 can be used to monitor molecular contamination in a variety of different environments, the operating temperature is preseleeted by the user depending on the environmental conditions of the area which is to be monitored. The temperature control electronics 30 produces a temperature signal which is representative of the temperature difference between the measured temperature and the stored preset temperature. This signal is output from the electronics 30 to a power supply 68. The temperature signal determines the magnitude and direction of a current delivery signal that is sent on line 70 from the power supply 68 to the thermoelectric element 56 to operate the thermoelectric element 56 in either the cooling or the heating mode.

If the environmental temperature is below the present temperature, the thermoelectric element 56 is operated in the heating mode. When the thermoelectric element 56 is operated in the heating mode, the current 70 which is applied to the thermoelectric element 56 produces heat, the level of which is dependent upon the magnitude of the current signal 70 which is applied to the thermoelectric element 56. The heat from the thermoelectric element 56 is transferred into the heat sink 46 which is in thermal contact with the thermoelectric element 56. The heat from the thermoelectric element 56 travels along the length of the heat sink 46 and eventually reaches the SAW resonators 22, 24. The SAW resonators 22, 24 are continuously heated by the thermoelectric element 56 via the heat sink 46 until the SAW resonators 22, 24 reach the desired preset temperature.

If the environmental temperature is above the present temperature, the thermoelectric element 56 is operated in the cooling mode. When the thermoelectric element 56 is operated in the cooling mode, the thermoelectric element 56 draws heat from the heat sink 46. The rate at which the heat is drawn from the heat sink 46 is dependent upon the magnitude of the current signal 70 which is applied to the thermoelectric element 56. The heat sink 46 is in thermal contact with the SAW resonators 22, 24 and therefore draws the heat from the SAW resonators 22, 24 and delivers it to the thermoelectric element 56 when it is operating in the cooling mode. The excess heat which is drawn by the thermoelectric element 56 is dissipated though the fins 62 of the radiator 60 which are cooled by an air stream entering the enclosure 34 of the NVR monitor 20 through an air vent 36. The air within the enclosure 34 is drawn out of the enclosure 34 through an external vent 38 by means of a blower 72. The external vent 38 is located in a back panel 74 of the NVR monitor 20 to ensure that the self-generated contaminants from the NVR monitor 20 are expelled in a direction which is away from the SAW resonators 22, 24 to prevent inaccurate NVR readings from occurring. The system control electronics 30 controls the operation of the blower 72 via line 71 to turn on the blower 72 when the thermoelectric element 56 is operated in the cooling mode and to turn off the blower 72 when the thermal electric element 56 is operated in the heating mode.

As described above, the heat sink 46 is positioned between the SAW resonators 22, 24 and the electronic circuit board 26 which contains the SAW control electronics. Electrical leads of the SAW resonators 22, 24 are connected through the heat sink 46 to the electronic circuit board 26 via an electrical path 76. As it is desirous to provide an NVR monitor 20 which is inexpensive to manufacture, in the preferred embodiment of the NVR monitor 20, the SAW resonators 22, 24 are located close to the circuit board 26 to eliminate the need for additional circuitry to compensate for the phase shifting, impedance mismatching and losses which may otherwise occur along the electrical path 76. However, it is also desirous to provide a heat sink 46 of sufficient thickness that the heat generated by the SAW resonators 22, 24, the external environment and the internal system control electronics 30 be dissipated as quickly as possible through the heat sink 46 and away from the SAW resonators 22, 24. Preferably, a heat sink 46 of at least 0.1 inches thick is used to provide a sufficient dissipation of the excess thermal energy. The preferred embodiment of the present invention utilizes a heat sink 46 which is approximately 0.25 inches thick. A recess 78 of approximate 0.05 inches in depth is formed in the heat sink so that the thickness of the heat sink at the recess is approximately 0.20 inches. The SAW resonators 22, 24 are mounted within the recess 78 of the heat sink 46. The preferred embodiment of the recess 78 has an area that is not substantially larger/than the combined area of the SAW resonators 22, 24 such that the heat sink 46 remains sufficiently thick through its length to provide good thermal conduction. Preferably, the length of the electrical path 76 between the SAW resonators 22, 24 and the circuit board 26 is approximately 0.1 to 0.2 inches in length.

The NVR monitor 20 outputs the data that it collects via a data port 79 to an external recording and/or processing system (not shown). Some examples of the types of data which are collected by the NVR monitor 20 are: the beat frequency from the sensing 22 and reference 24 resonators, which indicates the level of molecular contamination measured by the NVR monitor 20, the temperature of the SAW resonators 22, 24 as determined by the temperature sensor 64, the room temperature and the humidity of the environment as determined by the environmental sensors 44, etc. These data signals are collected and scaled to signal levels which are accepted by the external recording and/or processing system by signal conditioning electronics which are a part of the system control electronics 30 of the NVR monitor 20. These signals are output through the data port 79 to the external recording and/or processing systems for recording and or analysis.

Using the above described active temperature control of the SAW resonators 22, 24, the baseline noise level is typically ±1 Hz (measured with 1 Hz resolution). The lower limit-of-detection of the SAW resonator real-time NVR monitor 20 can be calculated using the mass sensitivity of $2 \times 10^{-11}$ gm/Hz cm$^2$ and an active area of 0.1 cm$^2$.

$$\frac{\Delta F}{\Delta m} = 2 \times 10^{-11} \frac{gm}{Hz\ cm^2} \times 0.1\ cm^2 = 2 \times 10^{-12} \frac{gm}{Hz} \quad (3)$$

The signal shift from the deposition of $1 \times 10^{-8}$ gm/cm$^2$ per month of NVR contamination would be:

$$\frac{1 \times 10^{-8}\ gm\ month^{-1}\ cm^{-2}}{2 \times 10^{-11}\ gm\ Hz^{-1}\ cm^{-2}} = 500\ Hz\ per\ month$$

or approximately 17 Hz/day, which corresponds to a signal/noise (S/N) of approximately 6 (assuming a ±1 Hz noise level and at least a S/N=3 for detection).

The high performance of a 200 MHz SAW resonator can be realized by comparison to a 10 MHz TQCM instrument. Assuming a NVR deposition of $1 \times 10^{-8}$ gm/cm$^2$ per month and the 10 MHz TQCM mass sensitivity of $4.42 \times 10^{-9}$ gm/Hz cm$^2$, the signal shift of a 10 MHz TQCM would be:

$$\frac{1 \times 10^{-8}\ gm\ month^{-1}\ cm^{-2}}{4.42 \times 10^{-9}\ gm\ Hz^{-1}\ cm^{-2}} = 2\ Hz\ per\ month$$

or 0.08 Hz/day.

In addition to maintaining an active temperature control independent of the temperature fluctuations, other precautions are taken to ensure an accurate NVR measurement is achieved. For example, the operational elements of NVR monitor 20 are enclosed in the enclosure 34 and the systems self-generated contaminants are directed away from the sensing resonator 22 when they are expelled from the enclosure to prevent contamination of the environment under monitoring.

Figure 5:
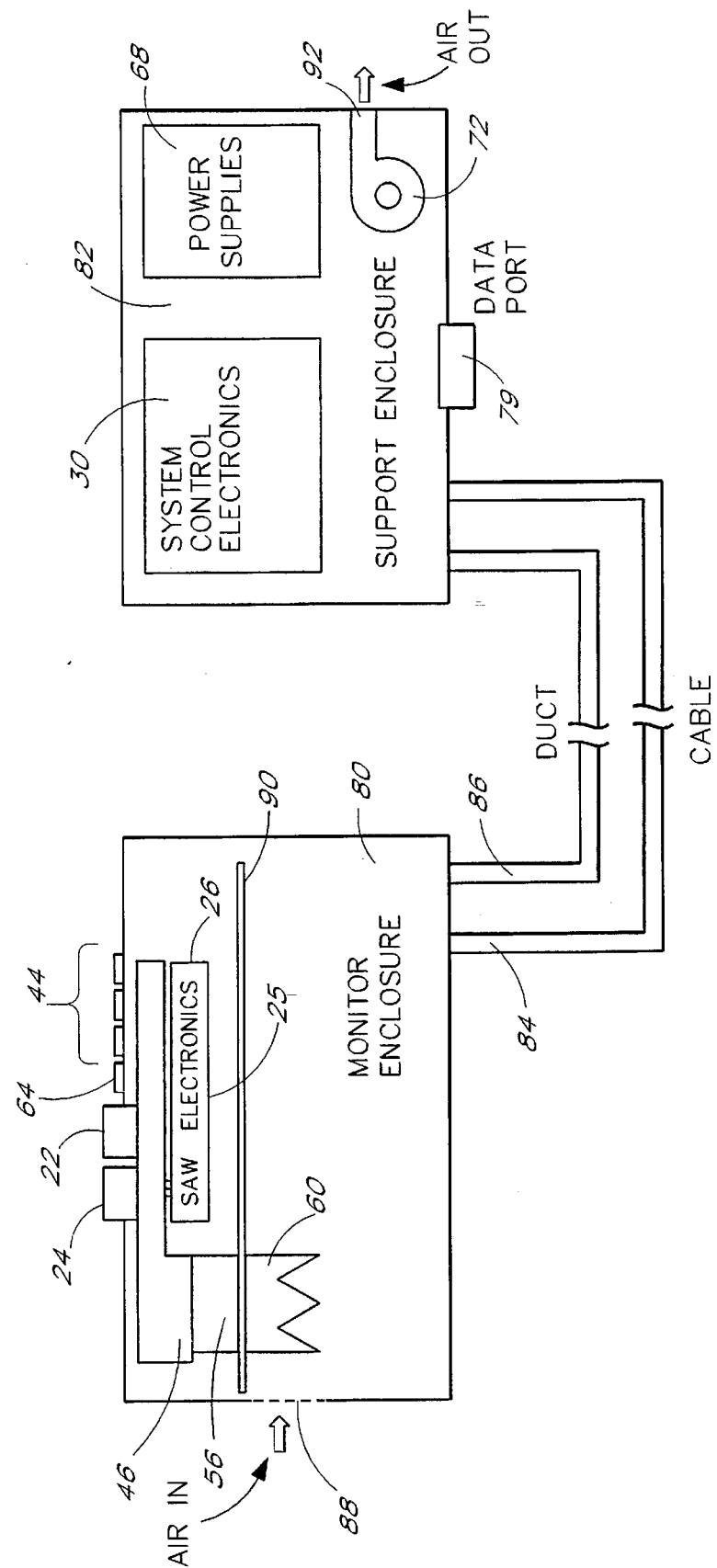
FIG. 5 is a schematic diagram of one alternate embodiment of the NVR monitor of the present invention.

In an alternate embodiment of the NVR monitor as illustrated in FIG. 5, the contamination producing elements of the NVR monitor are housed in a separated enclosure from the SAW resonators 22, 24. The SAW resonators 22, 24, the heat sink 46, the SAW electronics circuit board 26, the thermoelectric element 56 and the radiator 60 are all located in a monitoring enclosure 80. The system control electronics 30, such as the temperature control electronics, the signal conditioning electronics, etc., the data connection port 79, the power supplies 68 and blower 72 are located in a support enclosure 82. The monitoring enclosure 80 is located in the environment which is to be monitored and the support enclosure 82 is located in a remote location. The monitoring enclosure 80 and the support enclosure 82 are joined together with sealed cables 84 and ventilation duets 86, so as to further isolate the possible sources of contaminants from the environment under surveillance.

The monitoring enclosure 80 is sealed from the external environment except for an air vent 88 and a sealed ventilation duct 86. The airstream which enters the monitoring enclosure 80 though the air vent 88 is used to cool the radiator 60. In the alternate embodiment, this flow of air is shielded from the SAW resonators 22, 24 and the SAW electronics circuit board 26 by a heat shield 90. In addition, the heat shield 90 is used to maintain a steady temperature of the SAW resonators 22, 24 by preventing the hot air which is dissipated by the radiator 60 from contacting the SAW resonators 22, 24 and reheating them.

Fluids, such as air, are drawn from the monitor enclosure 80 into the support enclosure 82 via the sealed ventilation duet 86 by means of a blower 72 located in the support enclosure 82. The blower 72 also moves air through the interior of the support enclosure 82 to keep the support electronics 30 cool and exhausts the air though an external vent 92. The remote location of the support enclosure 82 and the ducting of the air from the monitor enclosure 80 to the support enclosure 82 ensures that the system's self generated contaminants would not be discharged in the vicinity of the location being monitored.

Figure 7:
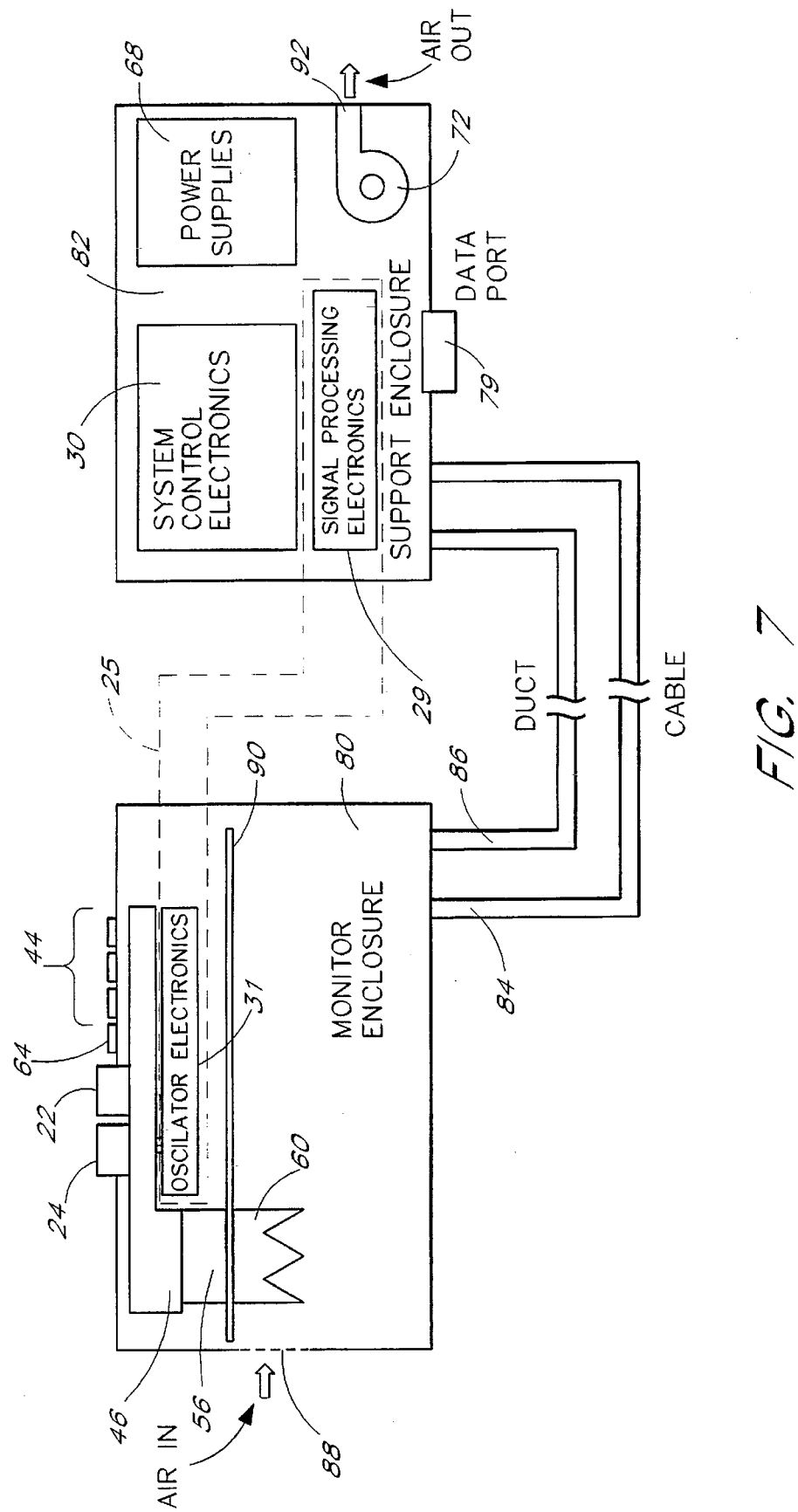
FIG. 7 is a schematic diagram of another alternate embodiment of the NVR monitor of the present invention.

Another configuration of the NVR monitor is shown in FIG. 7. In this configuration, the signal processing electronics 29 and the oscillator electronics 31 (which together make up the SAW control electronics 25) have been physically separated. More specifically, the signal processing electronics 29 which generate the majority of the heat have been moved to the support enclosure 82 with the system control electronics 30, the data connection port 79, the power supplies 68 and blower 72. The oscillator electronics 31 remain located in proximity to the heat sink 46 within the monitor enclosure 80. In one embodiment, the oscillator electronics 31 are connected to the signal processing electronics 29 by electrical conductors (e.g., wires) within the sealed cables 84. In another embodiment, the oscillator electronics 31 are connected to the signal processing electronics 29 by optical fiber. The fiber optics may be within the sealed cables 84 or may be located within a separate jacket or duct (not shown).

In order to evaluate the real-time NVR monitor 20 under actual operating conditions it was installed on one of the Test Stands in the O&C building at Kennedy Space Center as described below in Example 1.

EXAMPLE 1

In order to assure the SAW sensor's physical, thermal and air flow environment was similar to a standard NVR witness plate, the temperature controlled NVR monitor 20 was integrated onto an actual NVRR witness plate. The NVR plate containing the NVR monitor 20 was attached to one of the rails on the Test Stand. The SAW resonator real-time NVK monitor 20 operated unattended for 14 days in the O&C building. Several data were collected during this time: SAW beat frequency, NVR plate temperature, SAW temperature and the drive voltage of the thermoelectric element 56. The extremely high sensitivity of the SAW resonator 22, combined with its ability to detect very small levels of material flux (at a resolution in the fractional mono-molecular-layer range), allows one to observe and measure both volatile and non-volatile material fluxes (in either vapor or condensed form). Examination of the frequency shift versus time data obtained from the 14-day test revealed the simultaneous presence of non-volatile and volatile materials which are correlated to scheduled activities.

Figure 8:
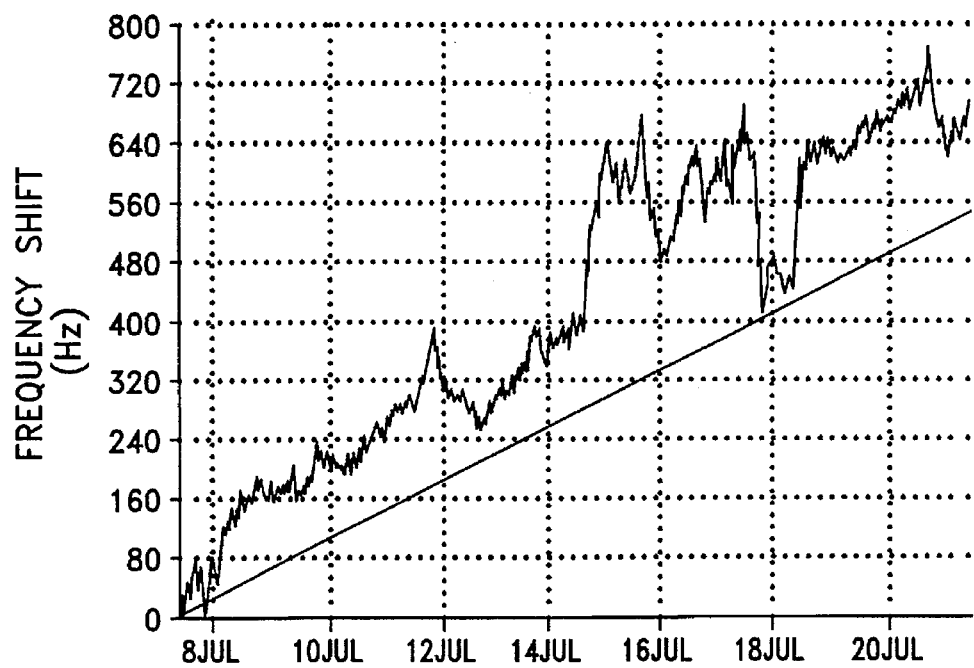
FIG. 8 is a graph of the change in beat frequency versus time during a fourteen day test of the NVR monitor of the present invention.

The change in the SAW sensor beat frequency versus time data from the 14 day on-site test is shown in FIG. 8. It can be seen that there is a general rising trend in the frequency over the test period, represented by the locus of the frequency trace, and corresponds to an average deposition rate of about 1 $ng/cm^2$ day. Superimposed on this rising slope are a number distinct signatures which are seen as rising and falling frequencies, indicating the arrival and departure of volatile materials as observed in our laboratory studies. These signatures can be correlated to activities occurring in the environment where the real-time NVR monitor 20 was located. Some parts of the volatile trace show a general rise with small decays, indicating the source, or sources were present during extended periods. There are also discrete events in which the deposition rate was very high; but these were nearly always followed by an equally steep decline, with a resulting peak that exhibits symmetry. This would be the result of some relatively strong volatile source being brought to the area and subsequently removed. There are also periods of sustained decay in the frequency for many hours. Examination of the timing would show that these were periods after the departure of a work crew. Details to which activities were logged varied considerably, so that it is not possible to correlate every notable frequency event with a known activity. However, all but two contamination episodes were correlated to scheduled activities on the Test Stand. Test Notes or other Kennedy Space Center documentation was not available to identify the two episodes.

Figure 9:
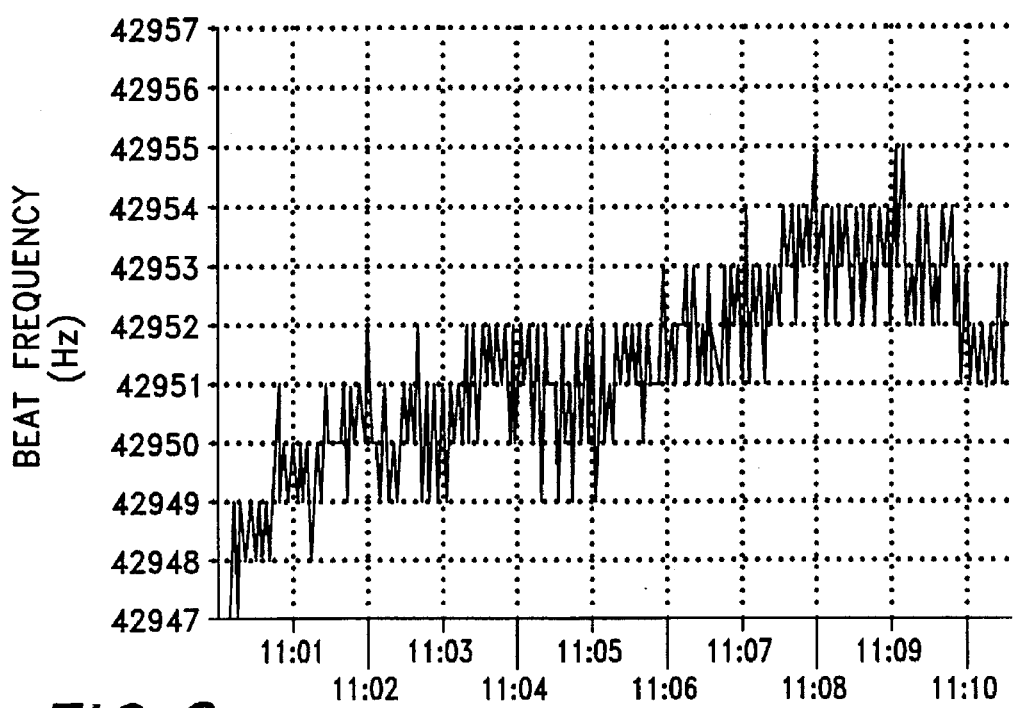
FIG. 9 is a graph of the raw data collected versus time over an eleven hour period of time during the testing of the NVR monitor of the present invention illustrating the baseline stability or noise associated with the temperature readings.

Due to the absence of major activities during the first week, an assessment of the typical baseline stability or "noise" is possible. An eleven hour segment of the raw data is expanded and shown in FIG. 9 (a data point is taken every 45 seconds). This plot illustrates the worst case thermally induced noise from the temperature controller is ±2 Hz, which corresponds to a lower-limit-of detection of 0.13 $ng/cm^2$, assuming a S/N of 3.

The temperature controlled SAW resonator real-time NVR monitor 20 operated flawlessly over the 14 day period at Kennedy Space Center and successfully measured less than 1 $ng/cm^2/day$ NVR contamination. Contamination episodes detected by the instrument were correlated with scheduled activities on the Test Stand. Assuming a baseline noise level of ±2 Hz (mainly thermally induced) the absolute mass lower limit of detection would be 0.13 nanograms/$cm^2$. This would enable the detection of a daily NVR deposition rate of less than 0.1 nanograms/$cm^2$/day.

The NVR monitor 20 has proven itself to be useful for space applications by measuring the NVR contamination in the O&C building at the Kennedy Space Center. In addition, the NVR monitor 20 can be advantageously used to measure the level of NVR contamination in "clean rooms" used in high technology manufacturing environments, such as in microelectronics manufacturing, high precision optical manufacturing, and in any other area where contamination on the molecular level is undesirable.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

We claim:

1. An apparatus for detecting contamination, comprising:
   a heat sink having opposing sides;
   a detection SAW resonator in thermal contact with one side of said heat sink;
   SAW control electronics, at least a portion of said SAW control electronics being in proximity to the other side of said heat sink, said portion of said electronics being electrically connected to said SAW resonator along an electrical path through said heat sink; and
   wherein there is no thermoelectric element in direct physical contact with said SAW resonator.

2. The apparatus of claim 1, wherein said electrical path is no more than 0.25 inches in length.

3. The apparatus of claim 1, wherein said electrical path is between approximately 0.1 inches and approximately 0.2 inches in length.

4. The apparatus of claim 1, wherein said SAW resonator resonates at a frequency of approximately 200 MHz–2,000 MHz.

5. The apparatus of claim 1, wherein said heat sink is L-shaped.

6. The apparatus of claim 5, additionally comprising a thermoelectric element in thermal contact with said heat sink, and a radiator in thermal contact with said thermoelectric element.

7. The apparatus of claim 5, additionally comprising a radiator and a thermoelectric element which heats and cools said heat sink, said radiator in thermal contact with said thermoelectric element, wherein said thermoelectric element and said radiator are mounted on one leg of said L-shaped heat sink, said SAW resonator is mounted to another leg of said L-shaped heat sink and said SAW control electronics are mounted proximal to said another leg of said L-shaped heat sink.

8. The apparatus of claim 1, additionally comprising first and second enclosures, said enclosures being separate from each other and being operatively connected to each other to transfer signals therebetween, one of said enclosures comprising a monitor enclosure which houses said SAW resonator, the other of said enclosures comprising a support enclosure which houses support devices, one of said support devices comprising a power supply.

9. The apparatus of claim 8, additionally comprising a duct between said first and second enclosures for drawing fluid from said monitor enclosure to said support enclosure.

10. The apparatus of claim 1, wherein said portion of said SAW control electronics in proximity to the other side of said heat sink comprises oscillator electronics.

11. The apparatus of claim 1, wherein another portion of said SAW control electronics is located remotely from said SAW resonator.

12. The apparatus of claim 11, wherein said another portion of said SAW control electronics comprises signal processing electronics.

13. The apparatus of claim 11, wherein said another portion of said SAW electronics is connected to said portion of said SAW control electronics in proximity to the other side of said heat sink by an electrical conductor.

14. The apparatus of claim 11, wherein said another portion of said SAW electronics is connected to said portion of said SAW control electronics in proximity to the other side of said heat sink by fiber optics.

* * * * *

UNITED STATES PATENT AND TRADEMARK OFFICE
CERTIFICATE OF CORRECTION

PATENT NO. : 5,661,226
DATED : August 26, 1997
INVENTOR(S) : William D. Bowers, et al It is certified that error appears in the above-identified patent and that said Letters Patent is hereby corrected as shown below:

```
Column 2, line 22 change "to Selker, et at." to --to Sekler, et al.--
Column 2, line 32 change "be manageable" to --be unmanageable--
Column 3, line 57 change "the NYR" to --the NVR--
Column 4, line 25 change "-fo²ΔM/A" to -- - afo²ΔM/A--
Column 5, line 40 change "cm²/gm" to --cm²--
Column 5, line 63 change "is dose to" to --is close to--
Column 8, line 22 change "in dose" to --in close--
Column 8, line 67, change "though" to --through--
Column 9, line 41 change "larger/than" to --larger than--
Column 9, line 43 change "through its" to --throughout its--
Column 10, line 48 change "duets 86" to --ducts 86--
Column 10, line 64 change "duet  86" to --ducts 86--
Column 10, line 54 change "though" to --through--
Column 10, line 67 change "though" to --through--
Column 11, line 33 change "NVRR witness" to --NVR witness--
Column 11, line 36 change "NVK monitor" to --NVR monitor--
```

Signed and Sealed this

Third Day of March, 1998

Attest:

BRUCE LEHMAN

*Attesting Officer*  *Commissioner of Patents and Trademarks*